United States Patent [19]
Schwan

[11] 3,991,059
[45] Nov. 9, 1976

[54] 2-METHYL-3-PHENYL-2,3,7,8,9,9α-HEXAHYDRO-1H-BENZ[DE] QUINOLINE

[75] Inventor: Thomas J. Schwan, Norwich, N.Y.

[73] Assignee: Morton-Norwich Products, Inc., Norwich, N.Y.

[22] Filed: May 12, 1975

[21] Appl. No.: 576,461

[52] U.S. Cl. .................. 260/283 R; 260/286 R; 260/573; 424/258
[51] Int. Cl.² .......................................... C07D 221/14
[58] Field of Search ............... 260/283 PF, 283 SY, 260/286 R

[56] References Cited
UNITED STATES PATENTS
3,575,984  4/1971  Plostnieks ..................... 260/283 SY OTHER PUBLICATIONS
Moser et al., J. Am. Chem. Soc. 81, pp. 2547–2550, (1959).
Bradsher, Chem. Review, vol. 38, pp. 463–471, (1946).
Schneider et al., Helv. Chem. Acta. vol. 56, pp. 759–773, (1973).
O'Brien et al., J. Chem. Soc. (1963) p. 2907–2917.
Schwan, J. Het. Chem., vol. 8(5), p. 839, (1971).

*Primary Examiner*—Nicholas S. Rizzo
*Assistant Examiner*—Mary C. Vaughn
*Attorney, Agent, or Firm*—Anthony J. Franze

[57] ABSTRACT

A compound 2-methyl-3-phenyl-2,3,7,8,9,9a-hexahydro-1H-benz [de] quinoline of the formula:

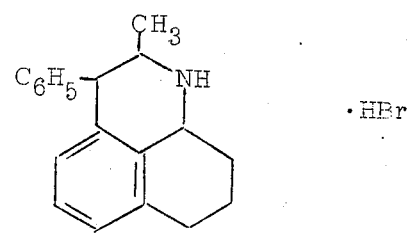

possesses pharmacological activity as an antidepressant.

1 Claim, No Drawings

2-METHYL-3-PHENYL-2,3,7,8,9,9 α-HEXAHYDRO-1H-BENZ[DE] QUINOLINE

This invention relates to chemical compounds. In particular it is concerned with a compound of the formula:

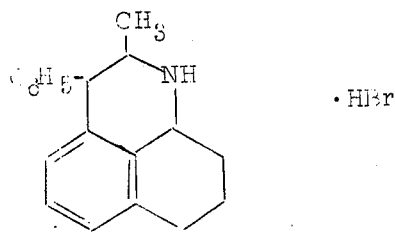

· HBr

This compound possesses pharmacological activity affecting the central nervous system. When administered perorally to animals it exhibits antidepressant action. Moreover, the chemical intermediate for this compound, 2-(1,2,3,4-tetrahydro-1-naphthylamino)-1-phenyl-1-propanol hydrochloride, also exhibits antidepressant action. The salt can be readily converted to the free base by treatment with base.

This antidepressant property is evidenced in the control of tetrabenazine-induced ptosis in mice. An oral dose of 50 mg/kg of these compounds to mice intraperitoneally receiving 35 mg/kg of tetrabenazine counteracts the ptosis-producing property of tetrabenazine.

In order that this invention be readily available to and understood by those skilled in the art the following illustrative examples are supplied:

EXAMPLE I

A.
2-(1,2,3,4-Tetrahydro-1-naphthylamino)-1-phenyl-1-propanol Hydrochloride

A mixture of 15.1 g (0.10 mole) 2-amino-1-phenyl-1-propanol free base, 14.6 g (0.10 mole) α-tetralone, 5.0 g p-toluenesulfonic acid monohydrate, and 250 ml toluene was stirred and refluxed using a Dean-Stark apparatus until the theoretical quantity of water had been collected (90 hour).

The mixture was stripped to a viscous oil which was dissolved in 300 ml CH$_3$OH. The solution was maintained at 25°–30° while sodium borohydride (7.6 g, 0.20 mole) was added over 15 minutes. The mixture was stirred at ambient temperature for 2 hours, stirred and refluxed for 30 minutes, then diluted with 400 ml H$_2$O. The mixture was extracted with 2 × 200 ml CHCl$_3$. The combined extracts were washed with 200 ml H$_2$O, dried (MgSO$_4$) and concentrated to dryness in vacuo to give an oil which was dissolved in 150 ml absolute ethanol. Ethanolic hydrogen chloride (75 ml) was added and the solution was concentrated to dryness. The solid was dissolved in 75 ml CH$_3$CN and upon cooling 10.0 g (31%) of the product, m.p. 182°–212°, was isolated. An analytical sample, m.p. 210°–212°, was obtained by recrystallization from isopropanol.

Anal. Calcd. for C$_{19}$H$_{23}$NO.HCl: C, 71.79; H, 7.61; N, 4.41. Found: C, 71.56; H, 7.48; N, 4.31.

EXAMPLE II

2-Methyl-3-phenyl-2,3,7,8,9,9a-hexahydro-1-H-benze[de]quinoline Hydrobromide

To 36.0 g (0.128 mole) of A, free base, was added cautiously 250 ml 48% HBr. The mixture was stirred and refluxed for 20 hours, cooled to room temperature, and filtered through a medium sintered glass funnel. The solid was air dried for 30 minutes, washed with 4 × 150 ml ethyl acetate, air-dried, and dried at 60° for 2 hours to give 21.5 g (49%) of the product, m.p. 252°–261°. An analytical sample, m.p. 257°–263°, was obtained by recrystallization from acetonitrile.

Anal. Calcd. for C$_{19}$H$_{21}$N.HBr: C, 66.28; H, 6.44; N, 4.07. Found: C, 66.48; H, 6.47; N, 3.91.

What is claimed is:
1. The compound of the formula:

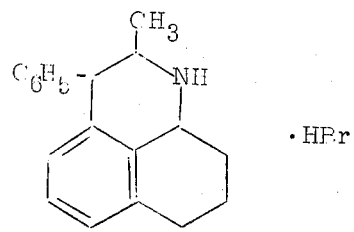

· HBr

* * * * *